United States Patent
Alfieri et al.

(10) Patent No.: US 7,674,286 B2
(45) Date of Patent: *Mar. 9, 2010

(54) ANNULAR PROSTHESIS FOR A MITRAL VALVE

(75) Inventors: Ottavio Alfieri, Brescia (IT); Francesco Maisano, Milan (IT); Alberto Redaelli, Milan (IT)

(73) Assignee: Edwards Lifesciences Corporation, Irvine, CA (US)

( * ) Notice: Subject to any disclaimer, the term of this patent is extended or adjusted under 35 U.S.C. 154(b) by 754 days.

This patent is subject to a terminal disclaimer.

(21) Appl. No.: 10/742,454

(22) Filed: Dec. 18, 2003

(65) Prior Publication Data

US 2005/0004666 A1    Jan. 6, 2005

Related U.S. Application Data

(63) Continuation of application No. 10/144,932, filed on May 15, 2002, now Pat. No. 6,726,717.

(30) Foreign Application Priority Data

May 17, 2001   (IT) .................. MI 2001A 1012

(51) Int. Cl.
*A61F 2/24*   (2006.01)
(52) U.S. Cl. .................... 623/2.36; 623/2.37
(58) Field of Classification Search ........... 623/2.36
See application file for complete search history.

(56) References Cited

U.S. PATENT DOCUMENTS

| 4,055,861 | A  | * | 11/1977 | Carpentier et al. ......... 623/2.36 |
| 5,607,471 | A  |   | 3/1997  | Seguin et al. |
| 6,019,739 | A  |   | 2/2000  | Rhee et al. |
| 6,102,945 | A  |   | 8/2000  | Campbell |
| 6,217,610 | B1 |   | 4/2001  | Carpentier et al. |
| 6,805,710 | B2 | * | 10/2004 | Bolling et al. ............. 623/2.36 |

OTHER PUBLICATIONS

Edwards Lifesciences, Carpentier-Edwards Classic Mitral Annuloplasty Ring, Feb. 12, 2001.
Advance in Mitral Valve Repair Using a Device flexible in Three Dimensions, ASAIO Journal vol. 42, No. 6, pp. 368-370, 1996.

* cited by examiner

*Primary Examiner*—Corrine M McDermott
*Assistant Examiner*—Christopher D Prone
(74) *Attorney, Agent, or Firm*—Rajiv Yadav, Esq.; Guy Cumberbatch, Esq.

(57) ABSTRACT

An annular prosthesis for a mitral valve that may include a posterior half-ring and an anterior half-ring coupled to each other on a first transverse plane which defines a maximum width section of the prosthesis. The ratio between the distance between the anterior half-ring and the posterior half-ring, as measured along a second plane, perpendicular to the first plane and equidistant to the couplings, and the maximum width of the prosthesis is lower than 3/4.

8 Claims, 1 Drawing Sheet

ANNULAR PROSTHESIS FOR A MITRAL VALVE

RELATED PATENT APPLICATIONS

The present application is a continuation of Ser. No. 10/144,932 filed May 15,2002, entitled ANNULAR PROSTHESIS FOR MITRAL VALVE, now U.S. Pat. No. 6,726,717, which claims foreign priority to Italian Patent Application Ser. No. MI2001a 001012, filed on May 17, 2001.

FIELD OF THE INVENTION

The present invention refers to an annular prosthesis for a mitral valve.

BACKGROUND OF THE INVENTION

A mitral plastic surgery operation includes a series of procedures suitable to re-establish the correct functionality of the mitral valve, when it is affected by congenital or acquired pathology. Among these procedures, the remodelling of the valve annulus is one of the most frequently used maneuvers in order to complete and/or to strengthen the valve. Remodeling provides for two moments: the reduction of the annular area and the proper remodeling that is suitable to re-establish the normal geometric ratios that are found in natural valves free of pathology. The first one of these maneuvers is usually carried out with the aid of a prosthesis that is appropriately sutured to the natural annulus. The prostheses for annuloplastic surgery available on the market are of two types. Flexible annular prostheses, made of various materials, that allow a "linear" reduction of the annular circumference, and rigid and semi-rigid annular prostheses made of various materials, that allow the "linear" reduction of the annular circumference and a geometric remodeling so as to re-establish the physiological systolic shape of the annulus. In the case of semi-rigid prostheses, they additionally allow a minimum deformation in order to allow the prosthesis to follow the deformations of the annulus-during the cardiac stages.

All the rigid and semi-rigid annular prostheses have a kidney-like or coupled D shape, with an anterior half-ring, rectilinear in first approximation, that gets sutured in correspondence of the joining of the anterior valve leaflet and a curved posterior half-ring that is sutured in correspondence of the joining of the posterior valve leaflet. The shape of the annular prostheses at issue reproduces the configuration of the valve annulus during the ventricular systole, and therefore in the stage of the valve closing. The ratio between the minor axis and the major axis is approximately 3/4 in all the models currently on the market, since this reproduces the normal anatomical ratios.

Recently the concept of undersizing of mitral valve annuloplasty has been introduced. This procedure is proposed in case of mitral insufficiency due to a reduced movement of the leaflets, as in the case of ischemic mitral valve or dilated cardiomyopathy. The undersizing consists in using a ring smaller than necessary, though still maintaining the ratio of approximately 3/4, and it is carried out in order to bring the base of the anterior leaflet even closer to the posterior leaflet in order to increase the coaptation surface (closure).

The Applicants noticed that in certain pathological conditions, there is a need to modify such ratio in order to make the operation of reconstruction of the mitral valve more effective: for instance in order to bring the valve leaflets closer to each other in the case of anatomical or functional tissue deficiency of one or both leaflets. In addition, it has also been observed that anatomical variation that do not correspond to the ratios reported above are frequent in nature.

In view of the state of the art described herein, the object of the present invention is to provide an annular prosthesis for mitral valve that can meet the different requirements that have been noticed.

SUMMARY OF THE INVENTION

According to present the invention, these and other objects have been attained by means of an annular prosthesis for a mitral valve made up of a posterior half-ring and an anterior half-ring that are coupled to each other on a first transverse plane which defines a maximum width section of the prosthesis. The ratio between the distance between the anterior half-ring and the posterior half-ring, as measured along a second plane, perpendicular to the first plane and equidistant to the couplings, and the maximum width of the prosthesis is lower than 3/4.

BRIEF DESCRIPTION OF THE DRAWINGS

The characteristics and the advantages of the present invention will become evident from the following detailed description of an embodiment thereof, which is illustrated by a non-limiting example in the enclosed drawings, in which.

DESCRIPTION OF THE PREFERRED EMBODIMENTS

Figure 1:
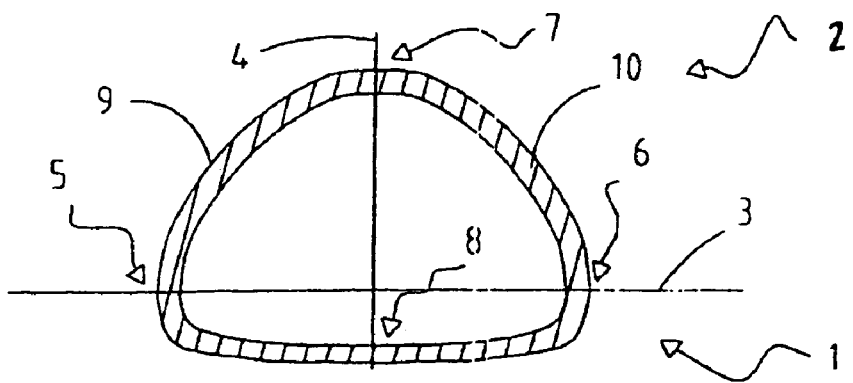
FIG. 1 shows an annular prosthesis for a mitral valve according to the known art.

In FIG. 1 a prosthesis for an annular mitral valve according to the known art is shown. It has a kidney-like or D-shape, and it is made up of an anterior half-ring 1 rectilinear in first approximation, that is sutured in correspondence of the joining of the anterior valve leaflet 1 and a curved posterior half-ring 2 that is sutured in correspondence of the joining of the posterior valve leaflet. The posterior half-ring 2 and anterior half-ring 1 are coupled at two points 5 and 6 located on a transverse plane 3 that define a maximum width section of the prosthesis. In addition a longitudinal plane 4 is defined that intersects the prosthesis at the points 7 and 8, and is arranged perpendicular to the transverse plane 3 and equidistant from the coupling points 5 and 6. The posterior half-ring 2 is thus subdivided in a first lateral zone (left) 9 located between the points 5 and 7, and a second lateral zone (right) 10 located between the points 6 and 7. The intersection points 5, 6 and 7, 8 of the prosthesis, respectively, with the planes 3 and 4 define the terms for the calculation of the dimensions of the prosthesis. According to the known art, the ratio between the distance between the points 7 and 8, herein also defined as the height of the prosthesis, and the distance between the points 5 and 6, herein also defined as the width of the prosthesis, is typically equal to 3/4.

Figure 2:
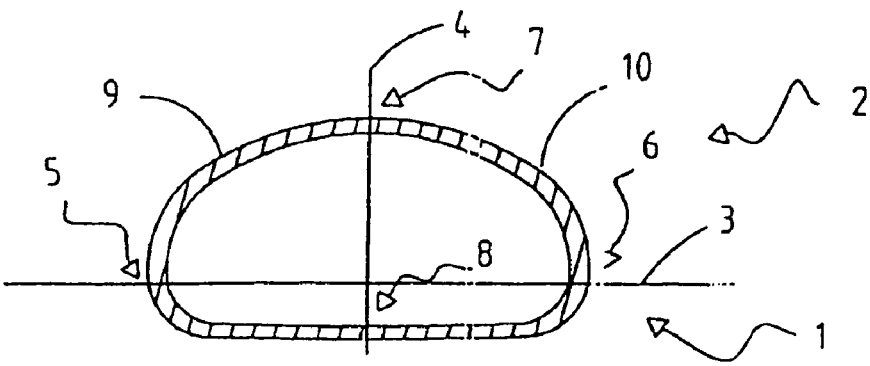
FIG. 2 shows a first embodiment of an annular prosthesis for a mitral valve according to the present invention.

In FIG. 2 a first embodiment of an annular prosthesis for a mitral valve according to the present invention is shown. It has substantially the same shape as the one rendered in FIG. 1, but the ratio between the height and the width of the prosthesis is lower than 3/4 (0.75), for instance equal to 2.5/4 (0.625) or equal to 2/4 (0.5).

For every size of prosthesis two or more reduced ratios can therefore be provided. By size, the dimension of the transverse width of the prosthesis is meant; it represents the clinical parameter on the basis of which the prosthesis is selected in each single clinical case in examination, and it is also the identifying parameter for the prosthesis.

The lower ratio, as compared with the prostheses currently used for annuloplastic surgery, allows its use in selected cases of pathologies that are not treatable in an adequate way with conventional prostheses.

The lower ratios in this case have the function to treat pathologies characterized by reduced movement of the leaflets with tethering (stretching towards the cardiac apex) symmetrical (as regards each leaflet) with medium or serious proportions. The reduction of the ratio confers the prosthesis a more "squeezed" shape that allows a better apposition of the leaflets in selected cases. For instance, in the dilated cardiomyopathy, when the expansion of the left ventricle determines a lateral movement and toward the apex of the papillary muscles, the leaflets stretch toward the cardiac apex and the apposition is thus lacking at the central level. Possible sizing, in addition, must respect an anatomical requirement: the anterior half-ring 1 (the base for the implant of the front leaflet) is anatomically fixed and not modifiable, and therefore, sizing should not be applied to this structure, that is, to the width of the prosthesis. The maintaining of a normal fore width of the prosthesis, associated with the reduction of the height allows an undersizing that is less inclined to deformation of the fore leaflet, therefore reducing the risk of residual insufficiency.

Figure 3:
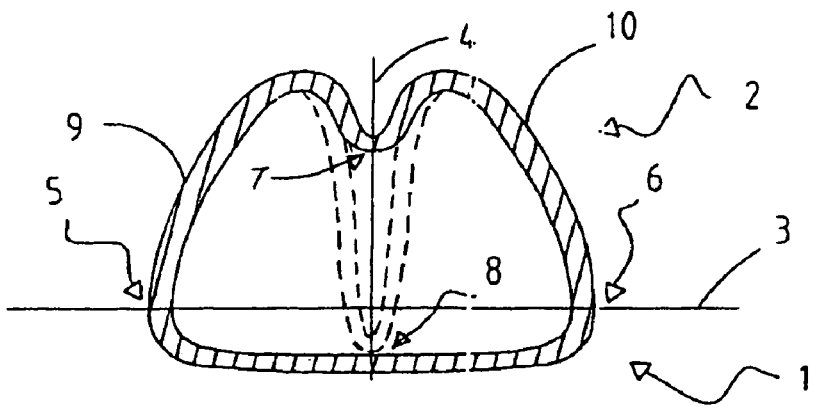
FIG. 3 shows a second embodiment of an annular prosthesis for a mitral valve according to the present invention.

In FIG. 3 a second embodiment of an annular prosthesis for a mitral valve according to the present invention is shown. In this case the natural ratio height/width of 3/4 is maintained in order to define the curving radii of the two lateral parts of the anterior half-ring. In the central zone, in proximity of the point 7, the distance between the posterior half-ring 2 and the front half-ring 1 is reduced, with the aim of obtaining a height/width ratio lower than 3/4. The central zone of the posterior half-ring 2 therefore takes a configuration that recalls the dog bone or gull wing shape and increases the coaptation at the central level by limiting the annular reduction at level of the commissure.

In some extreme cases, it could be useful to make the distance between the two half-rings in the central zone equal to zero, in order to obtain an eight-shape configuration, as seen in phantom in FIG. 3, in order to improve the coaptation at the central level. This remodeling simulates the double orifice operation, in which the leaflets are joined at the center of the valve in order to force the central coaptation. This prosthesis could also be used with this type of technique in order to reduce the stress on the suture and in order to minimize the reduction of the valve area.

Figure 4:
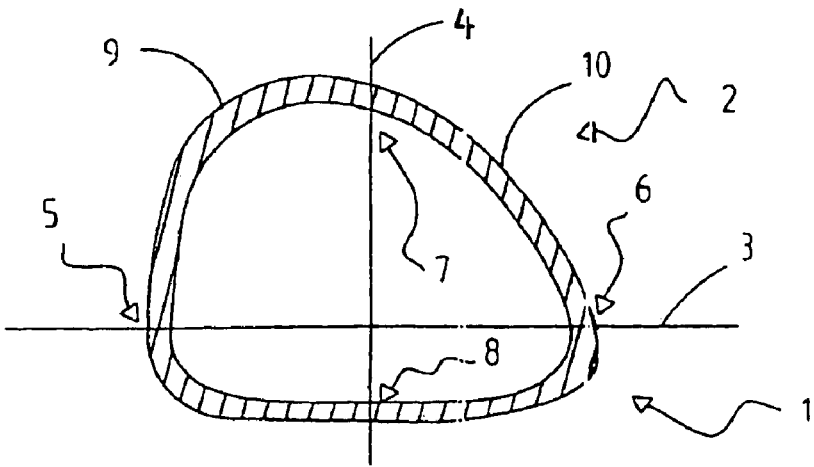
FIG. 4 shows a third embodiment of an annular prosthesis for a mitral valve according to the present invention.

In FIG. 4 a third embodiment of an annular prosthesis for a mitral valve according to the present invention is shown. In this embodiment the curving radius of one of the lateral zones, for instance the second lateral zone (right) 10, is increased so as to induce a selective increase of the competence in correspondence of the valve sector with reduced mobility of the leaflets (bad asymmetric apposition of the leaflets as in ischemic pathology). It is thus obtained that one part of the prosthesis, for instance the first lateral zone (left) 9, maintains a configuration substantially similar to the traditional prosthesis and one part, for instance the second lateral zone (right) 10, gets a sized configuration. In other words the distance between the middle point of the first lateral zone (left) 9 and the longitudinal plane 4 is greater than the distance between the middle point of the second lateral zone (right) 10 and the longitudinal plane The prosthesis, according to the present invention, can be made of an inert material that is highly tolerated by the human organism and can have a resistance that is appropriate to the use and that can substantially maintain the shape given to it.

What is claimed is:

1. An annular prosthetic ring for a mitral valve comprising:
    a curved posterior section contiguous with a generally rectilinear anterior section and together forming a generally D-shaped periphery oriented about a central flow axis, wherein in plan view as seen along the flow axis the ring has a major axis perpendicular to a minor axis, wherein a maximum dimension of the ring periphery lies along the major axis and a minimum dimension of the ring periphery lies along the minor axis, and wherein the posterior section has a central zone in which the posterior section bends inward toward the anterior section whereby the distance between the posterior section and the anterior section is reduced such that the posterior section abuts the anterior section.

2. The annular prosthetic ring of claim 1 wherein the distance between the posterior section and anterior section in the central zone is equal to zero.

3. A set of annular prosthetic rings for a mitral valve all having an identifying size, each ring comprising:
    a curved posterior section contiguous with a generally rectilinear anterior section and together forming a generally D-shaped periphery oriented about a central flow axis, wherein in plan view as seen along the flow axis the ring has a major axis perpendicular to a minor axis, wherein a maximum dimension of the ring periphery lies along the major axis and a minimum dimension of the ring periphery lies along the minor axis, and
    wherein the posterior section of a first ring in the set has a central zone in which the distance between the posterior section and the anterior section is reduced such that the posterior section abuts the anterior section.

4. The set of annular prosthetic rings of claim 3 wherein the central zone of the first ring in the set has a gull-wing shape.

5. The set of annular prosthetic rings of claim 3 wherein the the first ring has an eight-shape configuration.

6. The set of annular prosthetic rings of claim 3 wherein the distance between the posterior section and anterior section in the central zone of the first ring in the set is equal to zero.

7. The set of annular prosthetic rings of claim 6 wherein the distance between the posterior section and anterior section in the central zone in each of the rings in the set is equal to zero.

8. An annular prosthetic ring for a mitral valve comprising:
    a posterior section contiguous with an anterior section and together forming a periphery oriented about a central flow axis, wherein in plan view as seen along the flow axis the ring has a major axis perpendicular to a minor axis, wherein a maximum dimension of the ring periphery lies along the major axis, and a minimum dimension of the ring periphery measured perpendicular to the flow axis along a generally central portion of the ring lies along the minor axis, wherein the posterior section has a gull-wing shape wherein a central portion of the posterior section bends inwardly toward the anterior section such that the posterior section abuts the anterior section.

* * * * *

Disclaimer

7,674,286—Ottavio Alfieri, Brescia (IT); Francesco Maisano, Milan (IT); Alberto Redaelli, Milan (IT). ANNULAR PROSTHESIS FOR A MITRAL VALVE. Patent dated Mar. 9, 2010. Disclaimer filed July 15, 2010, by the assignee, Edwards Lifesciences Corporation.

The term of this patent shall not extend beyond the expiration date of Pat. No. 6,726,717.

*(Official Gazette, October 12, 2010)*